United States Patent [19]

Tustin et al.

[11] Patent Number: 4,853,480

[45] Date of Patent: Aug. 1, 1989

[54] OXYIODINATION INCORPORATING AN IODINE GENERATOR FOR THE CONVERSION OF METHYL IODIDE TO IODINE

[75] Inventors: Gerald C. Tustin, Kingsport, Tenn.; Kyle C. Smith, Nickelsville, Va.; Mark Rule, Kingsport, Tenn.

[73] Assignee: Eastman Kodak Company, Rochester, N.Y.

[21] Appl. No.: 82,300

[22] Filed: Aug. 6, 1987

[51] Int. Cl.$^4$ ............................................. C07C 69/76
[52] U.S. Cl. ..................................................... 170/100
[58] Field of Search ........................................ 560/100

[56] References Cited

U.S. PATENT DOCUMENTS 3,363,010 1/1968 Schwarzenbek .................... 560/100
4,240,987 12/1980 Martin et al. ........................ 560/100

FOREIGN PATENT DOCUMENTS 0171265 2/1986 European Pat. Off. .
0181790 5/1986 European Pat. Off. .
0183579 6/1986 European Pat. Off. .
57-77631 5/1982 Japan .
60-224644 11/1985 Japan .

OTHER PUBLICATIONS

Ogata, Y., J. Org. Chem. 34(12) 3974–7, 1969.

Primary Examiner—Paul J. Killos
Attorney, Agent, or Firm—Charles R. Martin; William P. Heath, Jr.

[57] ABSTRACT

A process for the vapor phase iodination of an aromatic compound which involves combusting an alkyl aromatic iodide in the presence of oxygen to produce molecular iodine and feeding the molecular iodine and an aromatic compound to an oxyiodination reaction to iodinate aromatic compounds.

10 Claims, No Drawings

OXYIODINATION INCORPORATING AN IODINE GENERATOR FOR THE CONVERSION OF METHYL IODIDE TO IODINE

BACKGROUND OF THE INVENTION

1. Field of the Invention

The invention relates to a methyl iodide combuster, and more particularly to a combuster used for the production of molecular iodine. The methyl iodide combuster may be operated upstream from an iodination reaction.

2. Discussion of the Background

Iodination reactions are used for preparing iodinated aromatic compounds. Typical aromatic starting materials are benzene, naphthalene and substituted analogs thereof. The iodinated aromatic compounds are useful as intermediates in the preparation of a variety of products, such as aromatic acids and esters through carbonylation reactions. Dicarboxylic acid esters of benzene and naphthalene are the preferred monomeric feedstocks for the production of polyester resins which are useful in the packaging and foodstuff industries.

Iodination reactions generally produce a mixture of iodinated isomers which must be separated so that the preferred isomer, for example, 2,6-diiodonaphthalene, can be carried through to other reactions, such as a carbonylation reaction. The undesired isomers are therefore side products and must be either discarded or recycled, with the latter being preferred. It is particularly important from an environmental and cost standpoint to recycle as much of the iodine which is present in the iodinated side products as possible. Additionally, it is desirable to recycle the iodine in a form that is useful as a feedstock for the iodination process itself, thereby allowing the process to be run in a continuous fashion.

At present, there is no known process which allows for the recycling of virtually 100% of the iodine incorporated in an alkyl iodide or iodoaromatic product to an iodination reaction in the form of molecular iodine. A need exists therefore for a process which can perform these operations.

SUMMARY OF THE INVENTION

Accordingly, one object of the present invention is to provide a process for the conversion of the iodine found in iodoaliphatic and iodoaromatic compounds into molecular iodine.

Another object of the present invention is to provide a process for converting iodinated products of an iodination reaction to molecular iodine.

A further object of the invention is a process for recycling the iodine found in the iodinated products of an iodination reaction back to the iodination reaction in the form of molecular iodine.

These and other objects which will become apparent from the following specification have been achieved by the present process for the iodination of an aromatic compound comprising the steps of (i) combusting an alkyl or aromatic iodide in the presence of a source of oxygen and an ignition source to produce molecular iodine and (ii) reacting the molecular iodine with an aromatic compound to produce an iodoaromatic compound.

BRIEF DESCRIPTION OF THE DRAWING

FIG. 1 illustrates a block diagram of the basic integrated unit according to the present invention.

FIG. 2 is a block diagram of an integrated unit including a carbonylation reactor with optional recycling of undesired aromatic iodides (ArI) and recycling of alkyl iodides from a carbonylation reactor (R'I) to the iodine generator.

FIG. 3 is a flow diagram of an oxyiodination reaction coupled with the iodine generator and a separation device.

DETAILED DESCRIPTION OF THE PREFERRED EMBODIMENTS

The process of the present invention utilizes a prereactor for the reaction of air or oxygen and an alkyl or aromatic iodide to produce molecular iodine and other combustion products. The output of the prereactor is mixed with an aromatic compound and optionally an additional source of oxygen and this mixture is fed directly to an iodination reactor. The use of a prereactor for the generation of iodine by combustion ensures total conversion of the alkyl or aromatic iodide to iodine and also allows for efficient removal of heat from the reaction.

The prereactor for the generation of iodine by combustion may be utilized to provide molecular iodine to any known iodination reaction. The iodination reaction may be a liquid phase reaction or a gas phase reaction, although the prereactor is preferably placed upstream from a gas phase iodination reactor. Typical liquid phase iodination reactors include those which utilize iodine and nitric acid or other strong acids and/or the presence of strong oxidants such as those disclosed in U.S. Pat. No. 4,240,987. Other iodination reactions which are suitable for use with the prereactor of the present invention include those disclosed in U.S. Pat. No. 3,363,010; EP No. 0 183 579; EP No. 0 181 790; EP No. 0 171 265; Japan No. 82/77631 and Japan 85/224644. Particularly preferred iodination processes are oxyiodination processes. The most preferred oxyiodination processes are those described in copending Application Ser. Nos. 912,806, filed Sept. 29, 1986; 028,959, filed Mar. 25, 1987; 028,898, filed Mar. 26, 1987; 029,897, filed Mar. 25, 1987; and 029,896, filed Mar. 25, 1987. The disclosures of these applications are incorporated herein by reference for a more complete description of the oxyiodination processes.

The invention will be further disclosed with reference to its use in conjunction with an oxyiodination reaction, a preferred embodiment, although the prereactor of the present invention is not limited to use with an oxyiodination reaction and in fact its use with any iodination reaction is expressly contemplated and shown in FIG. 1.

When an alkyl iodide is fed directly to an oxyiodination reactor, strong exotherms are produced causing difficulties in the control of the reaction. The reaction also produces small amounts of alkyl-substituted aromatic compounds in many cases. Additionally, significant portions of the alkyl iodides added often remain unreacted.

When the organic iodides are combusted in a prereactor, however, there are no strong exotherms produced in the oxyiodination reactor and alkylsubstituted aromatics are not produced. The use of a prereactor for burning organic iodides also ensures removal of trace organic impurities that might otherwise affect the oxiodination catalyst.

The prereactor or "iodine generator" uses an ignition source to initiate the combustion reaction. By "ignition source" is meant any means capable of initiating combustion of the organic iodide/oxygen mixture. Preferred examples of the ignition source are a flame, a spark or an electric arc. Also included within the term "ignition source" is any catalyst which is capable of catalyzing the combustion reaction. Suitable catalysts include the transition metals either unsupported or supported on an inert support. Preferred catalysts are the Group VIII transition metals or mixtures thereof. Particularly preferred are Pt, P, Rh, Fe and Ru and mixtures thereof. When a catalyst is used as the ignition source, temperatures of 170° to 1500° C. are generally used during the combustion reaction. The preferred temperatures range is 200° to 1000° C. Under these conditions, the combustion reaction is exothermic and therefore generates heat and becomes self-sustaining after it has been initiated.

By "source of oxygen" is meant a source of molecular oxygen ($O_2$) although other forms of oxygen such as ozone or atomic oxygen may be used. Preferred sources of oxygen are ari, oxygen in combination with an inert gas and enriched air. The most preferred source of oxygen is air.

The organic iodides which are combusted may be alkyl iodides or aromatic iodides. Alkyl iodides having 1-10 carbon atoms are preferred for use in the combustion reaction. The alkyl iodides may be straight-chained, branched or cyclic alkyl iodides. More preferred alkyl iodides are those having 1-4 carbon atoms with methyl iodide being most preferred. Aromatic iodides which are suitable for use in the combustion reaction include iodobenzenes, iodonaphthalenes and higher condensed ring iodoaromatics, with iodides of benzene and naphthalene being preferred. Volatile inorganic iodides, such as hydrogen iodide, ammonium iodide, or nitrogen iodides may also be utilized in the present invention.

When methyl iodide is used as the alkyl iodide, the reaction is believed to follow the following chemical equation:

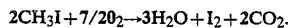

$$2CH_3I + 7/2O_2 \rightarrow 3H_2O + I_2 + 2CO_2.$$

In this equation, the reaction is shown as being stoichiometric with respect to molecular oxygen. While the use of a stoichiometric amount of oxygen is preferred, the combustion reaction may be run with less than or more than the stoichiometric amount of oxygen. When the reaction is run with excess oxygen, the reaction products are also water, molecular iodine and carbon dioxide. When the reaction is run with less than a stoichiometric amount of oxygen, additional combustion products can be detected. These additional combustion products include carbon monoxide and other organic species such as ethylene, ethane, and graphitic carbon.

The combustion products may be fed directly to the oxyiodination reactor without affecting the efficiency of the oxyiodination reaction. This is quite surprising since the increased gas flow through the oxyiodination reaction would be expected to dilute the reactant stream and therefore decrease the efficiency of the oxyiodination reaction. It is also surprising that the water, carbon dioxide, carbon monoxide and organic species which are passed to the oxyiodination reaction as impurities do not effect the efficiency of the oxyiodination reaction.

The present process, therefore, is a versatile and flexible means of recovering iodine from an oxyiodination reaction.

If desired, the graphitic carbon produced by the iodine combuster can be separated and recovered instead of passing the graphitic carbon to the oxyiodination reactor. This provides a convenient source of graphitic carbon for other industrial processes.

The aromatic compounds which can be utilized in the oxyiodination reaction are essentially any aromatic compound including substituted and unsubstituted aromatics. Suitable aromatic compounds include hydrocarbon aromatics, nitrogen containing aromatics, oxygen containing aromatics and sulfur containing aromatics. Typical hydrocarbon aromatics include benzene and biphenyl and condensed ring aromatics such as naphthalene and anthracene; sulfur containing aromatics include thiophene and benzothiophene; nitrogen containing aromatics include pyridine and benzopyridine, and suitable oxygen containing aromatics include furan and benzofuran. Other parent aromatics which may be used in the process of the invention include diaryl sulfones, diaryl ethers, diaryl carbonyls, diaryl sulfides and the like. Preferred parent aromatics are benzenes, biphenyls and naphthalenes. Substituents on the aromatic compounds which are suitable for the oxyiodination reaction include fluoro, chloro, bromo, iodo, hydroxy, and cyano groups. Aromatic compounds substituted by alkyl groups are generally not preferred. It has been found that with alkyl substituted aromatics the products are iodinated not only on the ring but also on the side chains. The side chain iodinated compounds represent side products which must be recycled to the iodine generator to recover the iodine incorporated within these compounds. Thus, while alkyl substituted aromatics can be utilized in the present technique their use is not preferred.

Catalysts which may be employed in the oxyiodination reaction are non-acidic catalysts, preferably zeolite catalysts. Preferred catalysts are those described in copending application Ser. Nos. 912,806, filed Sept. 29, 1986; 029,959, filed Mar. 25, 1987; 029,898, filed Mar. 25, 1987; 028,897, filed Mar. 25, 1987; and 029,896, filed Mar. 2, 1987 noted above.

The temperature at which the oxyiodination reaction is conducted is not critical and can be any temperature at which the aromatic compound is fluid. The maximum temperature at which the process can be carried out is that at which combustion of the aromatic compound occurs. Generally temperatures of from about 100° to 500° C. have been found satisfactory, with temperatures of from 200° to 400° C. being preferred. Most preferred temperatures are from about 200° to 350° C.

The pressure at which the process is conducted is not critical and can range from subatmospheric to superatmospheric. The utilization of elevated pressures in the gas phase process is preferable so as to minimize equipment size. In General, pressures from atmospheric to 600 psi have proven satisfactory although higher or lower pressures can be utilized.

The source of oxygen for the oxyiodination reaction can be any source of molecular oxygen such as, for example, pure oxygen, air or oxygen diluted with any other inert material such as carbon dioxide, water vapor, nitrogen gas or argon gas. Essentially molecular oxygen from any convenient source may be utilized. The purpose of the oxygen is to regenerate the active site on the catalyst to its active form once the iodination reaction has occurred. Thus, the amount of oxygen present during the reaction is not critical. However, it is preferred that at least ½ mole of oxygen be used for every mole of iodine. The molar ratio of iodine to aromatic compound which is to be reacted is largely determined by whether one desires to produce a monoiodinated aromatic product or polyiodinated aromatic product. Stoichiometrically, ½ mole of iodine reacts with 1 mole of aromatic compound to produce the monoiodinated form. Similarly, on a stoichiometric basis 1 mole of iodine is required to convert 1 mole of aromatic compound to the diiodinated form. Greater or lesser quantities of iodine can be utilized as the artisan may desire. In general, it is desired to run the process to obtain as close to 100% conversion of the iodine as practical so as to simplify the purification steps and to allow maximum recovery of the unreacted iodine. Preferred molar ratios of aromatic compound to iodine to oxygen are from 1:0.5:0.25 to about 1;2:3.

The source of iodine for the oxyiodination reaction is primarily the molecular iodine produced by the iodine generator. It is understood that some organic iodides may pass into the oxyiodination reactor if combustion in the iodine generator is incomplete. The presence of organic iodides does not interfere with the oxyiodination reaction and in fact organic iodides may serve as a separate source of iodine for the oxyiodination reaction. Therefore, essentially any source of iodine may be employed including molecular iodine ($I_2$), hydroiodic acid, alkyl iodides and aromatic iodides. The preferred source of iodine is $I_2$ produced by the iodine generator.

In one embodiment of the present process, the combustion products of the iodine generator are fed directly into the oxyiodination reaction in a continuous reaction stream. After separation from desired iodoaromatic products, the undesired organic iodides produced by the oxyiodination reaction can be recycled to the iodine generator and there combusted to regenerate molecular iodine and combustion products.

Alternatively the undesired iodoaromatic products from the oxyiodination reaction may be passed to an isomerization catalyst which is capable of redistributing the iodine among the product molecules. This redistribution is in effect a transiodination and is used to isomerize undesired isomers. The isomerization catalyst may be the same catalyst as the oxyiodination catalyst if desired. Preferred isomerization catalysts are those disclosed in copending applications Ser. Nos. 029,899, filed Mar. 25, 1987; 028,956, filed Mar. 25, 1987; and 028,949, filed Mar. 25, 1987. The disclosures of these applications are incorporated herein by reference for a more complete description of the isomerization and transiodination catalysts and reaction conditions.

The iodoaromatic products of the oxyiodination reaction may be recycled over the oxyiodination catalyst itself to effect isomerization or the products may be passed over a separate catalyst bed containing the isomerization catalyst. After isomerization, undesired iodoaromatic products may be recycled to the iodine generator in a manner similar to the recycling of iodoaromatic side products from the oxyiodination reaction described above, while the desired iodoaromatic products is further converted to useful product. The use of an isomerization catalyst bed improves the efficiency of the overall process by maximizing the production of the desired isomer. According, it is preferable to include an isomerization catalyst bed in the overall product reaction stream.

The process can be carried out as a continuous batch or semi-batch process. For example, the undesired iodoaromatic isomers produced by the oxyiodination reaction may be collected and isomerized and a portion of the isomerized product subsequently fed to the iodine generator as desired.

The separation of desired and undesired iodoaromatic isomers may be by a distillation column, a stripping column, an adsorption/desorption apparatus, or any other separation device which singly or in combination can adequately separate iodoaromatic isomers. A preferred adsorption/desorption apparatus is described in application Ser. No. 07/078665 filed July, 28, 1987 incorporated herein by reference.

The space velocity of the combined iodine generator and oxyiodination reactor processes is not critical and may be readily selector by the artisan. Hourly gas space velocities between about 10 and 15,000 preferably between 100–10,000 liters per hour of reagents per liter of active catalyst have proven satisfactory.

In a preferred embodiments, the desired iodoaromatic products of the oxyiodination reaction, such as for example, 2,6-diiodonaphthalene or p-diiodobenzene, are fed to a carbonylation reaction to produce aromatic carboxylic esters. Any suitable carbonylation reaction may be used, however the preferred carbonylation reactions are those disclosed in U.S. application Ser. Nos. 922,574, filed Oct. 22, 1986, and 922,594 filed Oct. 24, 1986. The disclosures of these applications are incorporated herein by reference for a more complete description of the carbonylation reaction conditions.

The alkyl iodide, preferably methyl iodide, produced by the carbonylation or other reaction can be recycled to the iodine generator for conversion to molecular iodine. This recycling provides efficient recapture of iodine. The methyl iodide is combusted as described above to produce molecular iodine which is then fed directly to the oxyiodination reaction.

In a most preferred embodiment, the iodine generator, oxyiodination reactor, and the carbonylation reactor are arranged as a continuous process with the methyl iodide from the carbonylation reaction being continuously recycled to the iodine generator. In this manner, the entire process can be run continuously with continuous recycling of iodine and the production of aromatic carboxylic esters. Of course, the entire process may be run batchwise or semi-batchwise although a continuous process is preferred.

Figure illustrates several possible embodiments as described above. An iodine generator is configured upstream from an iodination reactor. The iodine generator has an oxygen feed as well as an optional feed line for supplying alkyl or aromatic iodides from an outside source. The output from the iodination reactor is passed to a separation device where the desired products are separated and further passed to a carbonylation reactor for the production of aromatic carboxylic esters. The separation device may be configured with an isomerication catalyst bed to optimize the production of the desired isomeric product. Undesired reaction products from the iodination reactor, the separation device or the isomerization catalyst may be optionally recycled to the iodine generator to recover iodine, may be recycled to the iodination reactor or may be removed from the system for further outside processing. Although FIG. 2 illustrates a specific embodiment of the invention, the arrangement of the various components of the present invention will be determined by engineering considerations as well as the requirements of the particular products which are produced. The invention is therefore not limited to the embodiments illustrated in the Figures and discussed in the following examples.

Other features of the invention will become apparent in the course in the following descriptions of exemplary embodiments which are given for illustration of the invention and are not intended to be limiting thereof.

EXAMPLES

General

All examples illustrate iodine generation via methyl iodide combustion and subsequent oxyiodination of naphthalene. The apparatus used in the examples is an integrated unit consisting of gas flow controllers, (1a, 1b, 1c) methyl iodide vaporizer (2), naphthalene vaporizer (5), iodine generator (3), oxyiodination reactor (4), stripping column (6), underflow receiver (7), overhead receiver (8), and a toluene scrubber (9), A schematic diagram of the apparatus is presented in FIG. 3. Gas flow control is provided by maintaining a pressure drop across a capillary. Three separate air flow controls (1) are provided to the methyl iodide vaporizer (2), to the saturated gas stream exiting the methyl iodide vaporizer leading to the iodine generator (3), and to the naphthalene vaporizer (5). Methyl iodide is fed to the iodine generator (3) by the passage of a known amount of dry air from gas flow controller (1b) through the methyl iodide in the vaporizer (2) held at $-9°$ to $-12°$ C. by a circulating low temperature bath. Additional air required for the total combustion of methyl iodide is provided by the second air controller (1a). The methyl iodide air mix is fed to a 1-inch O.D. quartz manifold with separate arms for the iodine generator (3), naphthalene-air inlet, and outlet leading to the oxyiodination reactor (4). The iodine generator section of the manifold is contained in the upper vertical arm of the manifold and contains a thermowell, a 1-inch thick layer of quartz chips to disperse the reactant stream, a 3-inch layer of Davison Grade 701 automotive exhaust catalyst, and an additional layer of quartz chips to provide support for the automotive exhaust catalyst and mixing region for the iodine product with the naphthalene reactant. The entire manifold is electric heat-traced to prevent solidification of the naphthalene and iodine and to initiate the methyl iodide combustion. The iodine generator does not required additional heat once the combustion reaction is initiated.

Naphthalene is fed by passage of air provided by the third flow controller (1c) through molten naphthalene held at 175° to 180° C. by refluxing o-dichlorobenzene. The naphthalene-air mix is delivered to the horizontal arm of the manifold via an electric heat traced transfer line held at 225° C. The mix exiting the lower vertical arm of the manifold contains mostly iodine, naphthalene, air, water, $CO_2$, and residual nitrogen from the depleted air used in the iodine generator. The lower vertical arm of the manifold is connected directly to the top of the oxyiodination reactor. The oxyiodination reactor is a 1-inch O.D. quartz tube and is loaded with a 5-inch thick layer of quartz chips to heat the reactants, a 6 ½-inch thick layer (50 cm³) of 50% K-exchanged 1/8-inch extrudates 13X zeolite and a 1-inch layer of quartz chips to support the catalyst. A thermowell extends throughout the catalyst bed.

The output of the oxyiodination is fed to a stripping column (6). The stripping column is loaded with quartz chips and is electric heat-traced. Nonvolatile products are collected in an electric heat-traced underflow receiver (7). Volatile condensable products are collected in a steam-traced overhead receiver (8). The stripping column and underflow received are maintained at a temperature of 180° to 225° C. Heated nitrogen gas is fed to the bottom of the stripping column to facilitate the separatio. The material that is too volatile to condense in the overhead receiver is fed to a toluene scrubber. The scrubber (9) gases are then vented.

EXAMPLE 1

This example is typical of the standard operating conditions used in the integrated iodine generator naphthalene oxyiodination reaction process. The reaction is conducted at a barometric pressure of 735.9 mm Hg with the methyl iodide vaporizer held at $-9°$ C. and the naphthalene vaporizer held at 176° C. The inlet manifold, iodine generator, oxyiodination reactor furnace, stripping column, underflow receiver, and nitrogen purge stream are held 225°, 250°, 325°, 180°, 180°, and 180° C., respectively. Air is fed to the naphthalene vaporizer at a rate of 139 mL/min at STP. Air is fed to the methyl iodide vaporizer at a rate of 340 mL/min at STP and additional air is added to the saturated methyl iodide-air stream at a rate of 80 mL/min at STP. Nitrogen is fed to the base of the stripping column at a rate of 65 mL/min at STP. Shortly after the feeds are commenced, the temperature of the top of the iodine generator catalyst bed increases to 530° C. to 535° C., and this temperature is maintained throughout the entire reaction. The reaction is maintained for 62 minutes and the contents of both receivers and the scrubber are drained and discarded. The scrubber is loaded with fresh toluene and the reaction is continued for and additional 90 minutes. Both receivers and scrubber are drained, and the contents are analyzed by gas chromatography for organic products and the by thiosulfate titration for molecular iodine. The results of these analyses are presented in Table 1.

EXAMPLE 2

This example illustrates the operation of the process at low feed rates and low oxyiodination reactor temperature. The reaction is conducted at a barometric pressure of 734.4 mm Hg with the methyl iodide vaporizer held at $-9.5°$ C. and the naphthalene vaporizer held at 176° C. The inlet manifold, iodine generator, oxyiodination reactor furnace, stripping column, oxyiodination reactor furnace, stripping column, underflow receiver, and nitrogen purge stream are held at 225° C., 250° C., 225° C., 180° C., 180° and 180° C., respectively. Air is fed to the naphthalene vaporizer at a rate of 69 mL/min at STP. Air is fed to the methyl iodide vaporizer at a rate of 241 mL/min at STP, and additional air is added to the saturated methyl iodide air stream at a rate of 41 mL/min at STP. Nitrogen is fed to the base of the stripping column at a rate of 65 mL/min at STP. Shortly after the feeds are commenced, the temperature of the top of the iodine generator catalyst bed increases to 331° C. and this temperature is maintained throughout the entire reaction. The reaction is maintained for 60 minutes, and the contents of both receivers and the scrubber are drained and discarded. The scrubber is loaded with fresh toluene and the reaction is continued for an additional 131 minutes. Both receivers and scrubber are drained, and the contents are analyzed by gas chromatography for organic products and by thiosulfate titration for molecular iodine. The results of these analyses are presented in Table 2.

EXAMPLE 3

This example illustrates the operation of the process of low feed rates and 325° C. oxyiodination reactor temperature. The reaction is conducted at a barometric pressure of 734.4 mm Hg with the methyl iodide vaporizer held at −9° C. and the naphthalene vaporizer held at 176° C. The inlet manifold, iodine generator, oxyiodination reactor furnace, stripping column, underflow receiver, and nitrogen purge stream are held at 225°, 250°, 325°, 180°, 180° and 180° C., respectively. Air is fed to the naphthalene vaporizer at a rate of 75 mL/min at STP. Air is fed to the methyl iodide vaporizer at a rate of 241 mL/min at STP, and additional air is added to the saturated methyl iodide air stream at a rate of 41 mL/min at STP. Nitrogen is fed to the base of the stripping column at a rate of 65 mL/min at STP. Shortly after the feeds are commenced, the temperature of the top of the iodine generator catalyst bed increases to 331° to 333° C. and this temperature is maintained throughout the entire reaction. The reaction is maintained for 60 minutes, and the contents of both receivers and the scrubber are drained and discarded. The scrubber is loaded with fresh toluene and the reaction is continued for an additional 60 minutes. Both receivers and scrubber are drained, and the contents are analyzed by gas chromatography for organic products and by thiosulfate titration for molecular iodine. The results of these analyses are presented in Table 3.

TABLE 1

|  | Overhead Receiver | Underflow Receiver | Scrubber Solution |
|---|---|---|---|
| Product Isolated, g | 43.0 | 24.9 | 498 (includes toluene) |
| Composition, wt % |  |  |  |
| naphthalene | 50.2 | 0 | 1.4 |
| 2-iodonaphthalene | 31.9 | 25.6 | 0.1 |
| 1-iodonaphthalene | 16.0 | 12.8 | 0.1 |
| 2,7-diiodonaphthalene | 0.7 | 11.0 | — |
| 2,6-diiodonaphthalene | 1.0 | 21.5 | — |
| other diiodonaphthalenes | 2.4 | 20.0 | — |
| triiodonaphthalenes | 0 | 0.1 | — |
| iodine | 5.5 | 0.11 | 0.71 |

TABLE 2

|  | Overhead Receiver | Underflow Receiver | Scrubber Solution |
|---|---|---|---|
| Product Isolated, g | 31.3 | 11.4 | 784.0 (includes toluene) |
| Composition, wt % |  |  |  |
| naphthalene | 55.5 | 0 | 0.5 |
| 2-iodonaphthalene | 25.5 | 16.8 | — |
| 1-iodonaphthalene | 7.1 | 8.2 | — |
| 2,7-diiodonaphthalene | 0.8 | 21.2 | — |
| 2,6-diiodonaphthalene | 0.1 | 16.5 | — |
| other diiodonaphthalenes | 1.4 | 24.8 | — |
| triiodonaphthalenes | 0 | 6.8 | — |

TABLE 2-continued

|  | Overhead Receiver | Underflow Receiver | Scrubber Solution |
|---|---|---|---|
| iodine | 13.5 | 0.04 | 0.46 |

TABLE 3

|  | Overhead Receiver | Underflow Receiver | Scrubber Solution |
|---|---|---|---|
| Product Isolated, g | 18.7 | 8.5 | 508.9 (includes toluene) |
| Composition, wt % |  |  |  |
| naphthalene | 59.1 | 0 | 0.3 |
| 2-iodonaphthalene | 30.7 | 53.3 | — |
| 1-iodonaphthalene | 14.5 | 22.8 | — |
| 2,7-diiodonaphthalene | 0.5 | 6.8 | — |
| 2,6-diiodonaphthalene | 0.5 | 8.9 | — |
| other diiodonaphthalenes | 0.5 | 15.5 | — |
| triiodonaphthalenes | 0 | 2.7 | — |
| iodine | 0.99 | 0.09 | 0.04 |

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by letters patent of the United States is:

1. A process for the iodination of an aromatic compound, comprising the steps of:
   (i) combusting a $C_{1-10}$ alkyl or $C_{6-20}$ aromatic iodide in the presence of a source of oxygen and an ignition source, to produce molecular iodine, and
   (ii) oxyiodinating a hydrocarbon, nitrogen-containing, oxygen-containing or sulfur-containing aromatic compound at a temperature of about 100° to 500° C. in the presence of molecular oxygen, a non-acid catalyst and said iodine, to produce said iodinated aromatic compound.

2. The process of claim 1, wherein said source of oxygen is air, oxygen mixed with an inert gas, or enriched air.

3. The process of claim 1, wherein said ignition source is selected from the group consisting of a flame, a spark, an electric arc and a catalyst.

4. The process of claim 3, wherein said catalyst is an unsupported transition metal or a transition metal supported on an inert support.

5. The process of claim 4, wherein said transition metal is a Group 8 metal.

6. The process of claim 5, wherein said transition metal is selected from the group consisting of Pt, Pd, Rh, Ru, Fe, and mixtures thereof.

7. The process of claim 1, wherein said combusting reaction is conducted at a temperature from about 170°–1500° C.

8. The process of claim 7, wherein said combusting temperature is conducted at a temperature between about 200°–1000° C.

9. The process of claim 1, wherein the products of said combusting step are fed directly to said reacting step.

10. The process of claim 1, wherein said non-acid catalyst is a zeolite.

* * * * *